United States Patent
Szabo

(10) Patent No.: US 6,764,490 B1
(45) Date of Patent: Jul. 20, 2004

(54) SURGICAL TREATMENT TOOL FOR CREATING A RECESS IN A CARTILAGE AND/OR BONE TISSUE FOR A JOINT PROSTHESIS

(75) Inventor: Zsolt Szabo, Munich (DE)

(73) Assignee: Muller Erich Johann, Leinwallstadet (DE)

( * ) Notice: Subject to any disclaimer, the term of this patent is extended or adjusted under 35 U.S.C. 154(b) by 133 days.

(21) Appl. No.: 10/130,167
(22) PCT Filed: Nov. 7, 2000
(86) PCT No.: PCT/EP00/10985
§ 371 (c)(1), (2), (4) Date: Sep. 24, 2002
(87) PCT Pub. No.: WO01/34039
PCT Pub. Date: May 17, 2001

(30) Foreign Application Priority Data

Nov. 8, 1999 (DE) .......................... 199 53 611

(51) Int. Cl.$^7$ ............................... A61B 17/16
(52) U.S. Cl. ....................................... 606/81
(58) Field of Search .................. 606/79–81, 82–86

(56) References Cited

U.S. PATENT DOCUMENTS 5,116,165 A * 5/1992 Salyer .......................... 407/54
5,203,653 A * 4/1993 Kudla ......................... 408/207
5,376,092 A * 12/1994 Hein et al. ..................... 606/81
6,221,076 B1 * 4/2001 Albrektsson et al. ......... 606/80

FOREIGN PATENT DOCUMENTS

GB 2321598 * 8/1998 ........... A61B/17/16

* cited by examiner

Primary Examiner—Kevin Shaver
Assistant Examiner—Michael B. Priddy
(74) Attorney, Agent, or Firm—J.C. Patents

(57) ABSTRACT

A surgical tool to create a recess for an artificial joint in cartilaginous and/or bony tissue, and particularly for an artificial acetabulum in a hip-joint bone, is described which has an essentially hemispherical superficies 10 and a hollow interior space 50 bounded by this surface where at the superficies 10 are formed at least one cutting edge 20 extending from the pole 12 of the superficies 10 to the equator 14 of the superficies 10 and having at least one cutting element 20 with one cutting surface 26 turned toward the workpiece and one cutting surface 28 turned away from the workpiece, as well as one opening 22 in the superficies 10 cooperating therewith to evacuate the chips toward the hollow interior space 50, where for rotation around the axis of symmetry which forms the axis of rotation, a bearing shaft 40 extending through the hollow internal space 50 is fastened at the superficies 10 and where a clearance angle γ of the cutting edge 20 subtended between the superficies 10 and the cutting surface 26 of the cutting element 20 turned toward the workpiece decreases from the pole 12 of the superficies 10 toward the equator 14 of the superficies 10.

22 Claims, 3 Drawing Sheets

Figure 1:
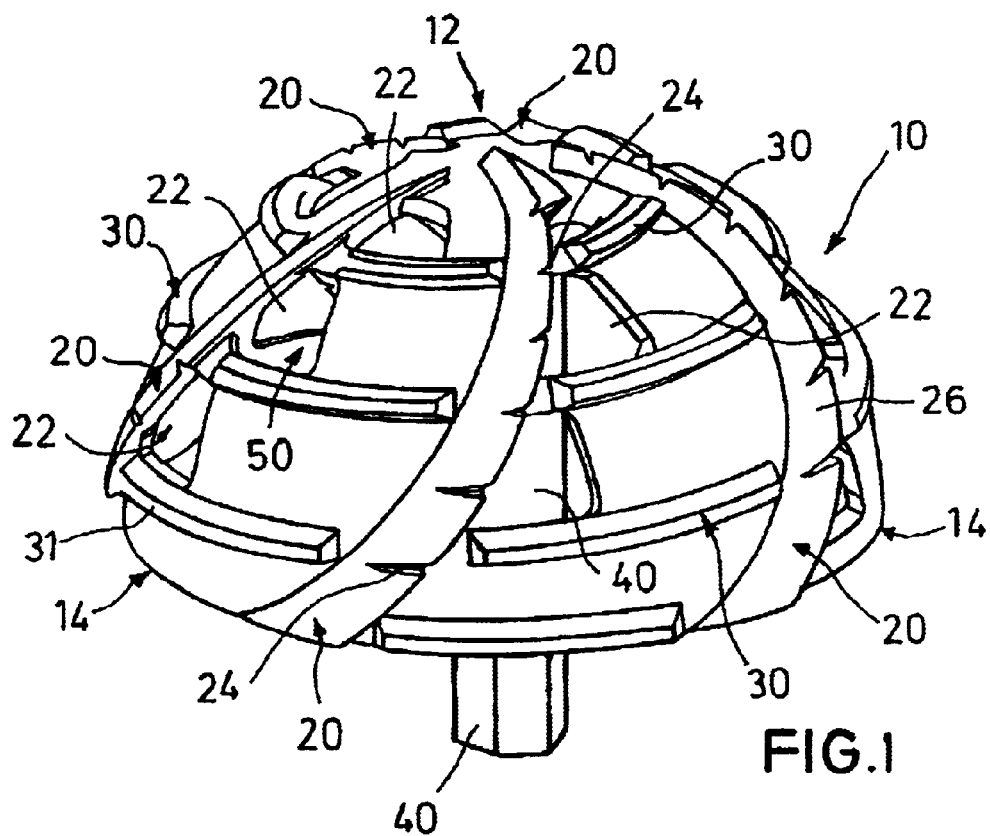

SURGICAL TREATMENT TOOL FOR CREATING A RECESS IN A CARTILAGE AND/OR BONE TISSUE FOR A JOINT PROSTHESIS

The invention concerns a surgical tool to create a recess for an artificial joint in cartilaginous and/or bony tissue, and particularly for an artificial acetabulum in hip-joint bones, having an essentially hemispherical superficies and a hollow interior space bounded by this superficies where are formed in the superficies at least one cutting edge extending from the pole of the superficies to the equator of the superficies and having at least one cutting element (20) with a cutting surface (26) turned toward the workpiece and one cutting surface (28) turned away from the workpiece, as well as one opening in the superficies cooperating therewith to evacuate the chips toward the hollow interior space, a bearing shaft for rotation about the axis of symmetry forming the axis of rotation being fixed at the superficies and extending through the hollow interior space.

Such a surgical tool is known from WO 95/13749 disclosing a tool to form a recess in a hip-joint acetabulum which has a hemispherical tool head. This tool head has several cutting edges and openings cooperating therewith through which the material to be removed is carried away to a hollow interior space in such a way that the machining process need not be interrupted because of material having been removed.

A tool for machining bones having a hemispherical head which inclusive of the cutting edges is made of plastic material is further disclosed in EP 0 574 701 A1. A particularly economic fabrication of the tool thus becomes possible, and with it single-use applications. This document moreover discloses an embodiment of the tool having a cutting edge surrounding the shaft in a helical manner and built up from a plurality of cutting elements.

A surgical milling cutter to insert prostheses which has a hemispherical tool head and a bearing shaft to be attached with the aid of a connecting piece and wherein the tool head has a central cutting element guiding the milling cutter as well as a plurality of cutting elements distributed over the hemispherical tool head is further disclosed in EP 0 782 840 A1.

However, such tools have the disadvantage that the hemispherical tool head yields a rate of removal of material which, because of increasing cutting speed, increases toward the periphery or equator. This causes the geometric shape of the recess to depart from the hemispherical cofiguration needed for the prosthesis. As a consequence, poor fit develops between the recess and the artificial acetabulum being received therein. This leads to shorter replacement intervals for the prosthesis, implying that the patient must submit to an intervention in relatively short time intervals in order to have implanted a new prosthesis.

It is an task of the present invention, therefore, to create a surgical tool forming a recess in a cartilaginous and/or bony tissue, and particularly for an artificial acetabulum in hip-joint bones, which enables a recess having the most precise geometric shape possible to be produced.

This task is resolved with a surgical tool according to the preamble of claim 1, by having a clearance angle $\gamma$ of the cutting element subtended between the superficies and the cutting surface turned toward the workpiece that decreases from the pole of the superficies toward the equator of the superficies.

By having a decreasing clearance angle $\gamma$ the speed of removal of material decreases toward the periphery or equator of the hemisphere in such a way that the geometric shape of the recess will almost exactly correspond to the shape of the hemispherical tool. Because of the precise configuration of the hemispherical recess, a better fit between the artificial acetabulum and the recess is attained so that the lifetime of the inserted prosthesis will increase. It follows that the time intervals between interventions during which a new prosthesis must be inserted into the patient become longer.

Moreover, in the tool according to the invention, the tendency to drift is reduced as compared to conventional tools by its clearance angle decreasing toward to periphery of the tool, since compared to conventional tools, the highest cutting efficiency of the tool according to the invention is closer to the pole of the superficies. As a result, the tool according to the invention, as compared to conventional tools, is autocentering during the machining when appropriately advanced in the direction of the axis of rotation.

Further advantageous embodiments of the invention are subjects of the dependent claims.

Through an extension, fabrication of the tool is particularly simple, especially in cases where the cutting edge is composed of a plurality of cutting elements.

An extension makes it possible to further improve the cutting behavior of the tool, since the clearance angle $\gamma$ is continuously adapted as a function of distance from the axis of rotation.

An extension has the advantage that the tool has an essentially uniform cutting performance throughout the cutting zone since the largest depth of advance $h_c$ of the cutting edge is constant over the entire cutting periphery, in such a way that the cutting characteristics of the tool are optimized. The largest depth of advance $h_c$, of the cutting edge is calculated from the equation: $h_c = 2\, r\pi \tan \gamma$, from which it can be seen that there is an indirect proportionality between the distance of the cutting edge from the axis of rotation and the value of $\tan \gamma$, the clearance angle $\gamma$ having values between 0° and 90°, i.e., the clearance angle $\gamma$ decreases when the distance between cutting edge and axis of rotation increases.

Through an extension, the volume of material removed can be adapted as a function of the radius, in which case the clearance angle $\gamma$ of the cutting element and the rake angle $\alpha$ of the cutting element are advantageously adjusted with respect to the material being cut.

Beyond that, the extension has the advantage that the effective cutting length of the cutting edge increases, since during the removal of material, in addition to the shearing force in the direction of rotation, an additional component of the shearing force appears in an outward direction so that material can be removed with a smaller effort.

An extension has the advantage that during the cutting operation, the tool is stabilized by the fact that several cutting edges are operative at once, so that the tool will hardly depart from the desired axis of rotation. Moreover, vibrations of the tool are reduced, so that the surface quality of the recess produced is improved.

Through an extension, an advantageous stabilization and a damping of the vibrations is brought about while the tool can be fabricated at a favorable price. Moreover, at least three cutting edges are operative within the same perimeter so as to secure structural stability.

An extension guarantees, moreover, that the notches serve as chip breakers, so as to reduce the risk of seizing of the tool in the workpiece.

The extension has the advantage, moreover, that the tool is guided by a guiding element having cutting functions when in contact with the workpiece, so that vibrations between the workpiece and the tool are reduced. The tool furthermore is reinforced against mechanical deformation, in such a way that the shape of the tool is not impaired during the cutting operation.

In an extension, the tool is guided along the entire superficies during the cutting operation, since the helical guiding element scans the entire superficies during one revolution.

The extension yields an additional radial or helical cutting edge further boosting the cutting performance of the tool, since the amount of material effectively removed, and the evacuation of the chips, is further increased. It is particularly advantageous when the clearance angle γ of the helical cutting edge that is subtended between the superficies and the cutting surface of the cutting element that is turned toward the workpiece decreases from the pole of the superficies toward the equator of the superficies. It is further possible to save material when fabricating the tool, as the openings between cutting edges and the helical opening overlap in such a way that the superficies of the tool essentially consists, merely of the cutting edges and the helical cutting edge.

Through an extension, the tool is additionally reinforced against mechanical deformation, since the cutting edges are multiply supported by the helix. Moreover, the points of intersection of the helix with the cutting edges serve as chip breakers.

Further details, features, and advantages of the invention will become apparent from the following description of an advantageous embodiment of the invention with the aid of the drawings.

Figure 2:
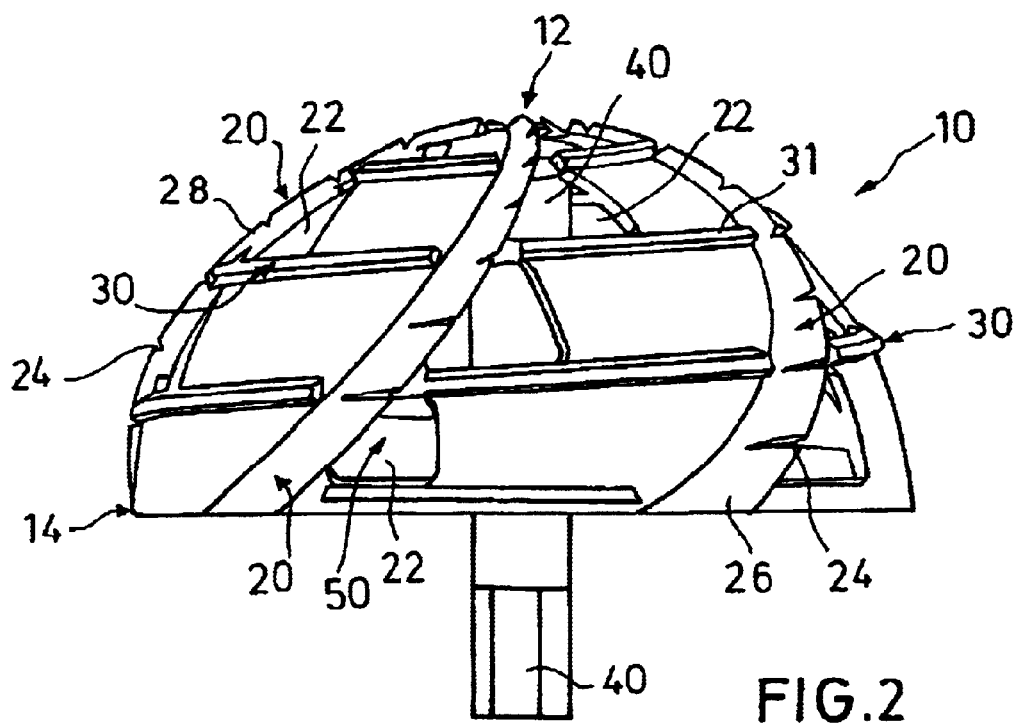
Figure 3:
Figure 4:
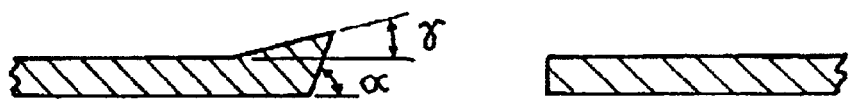
Figure 5:
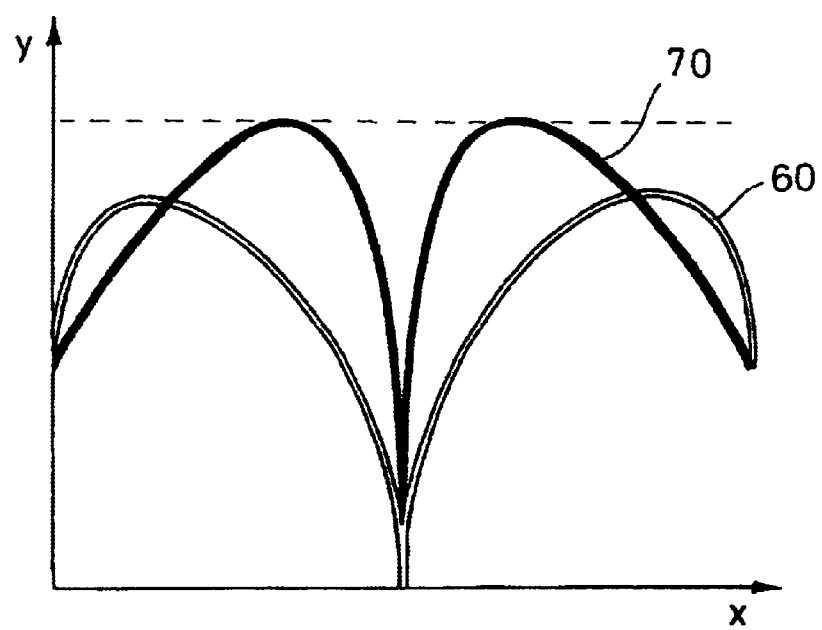

Shown are in:

FIG. 1 a perspective view of an embodiment of a tool in accordance with the invention;

FIG. 2 a lateral view of the embodiment of FIG. 1;

FIG. 3 a sectional view of a cutting element in the zone of the pole of the superficies of the tool of FIGS. 1 and 2;

FIG. 4 a sectional view of the cutting element in the zone of the equator of the superficies of the tool of FIGS. 1 and 2; and FIG. 5 a graphical representation of the cutting performance in relation to the diameter of cutting tools.

FIG. 1 presents an advantageous embodiment of a surgical tool according to the present invention having a hemispherical tool head 10 in the shape of a hemispherical superficies 10 and a hollow interior space 50 bounded thereby. At the hemispherical superficies 10, five cutting edges 20 are arranged which extend from the pole 12 of the superficies 10 to the equator 14 of the superficies 10, the cutting edges 20 being uniformly distributed over the superficies 10, and helically bent so that the cutting edges 20 reflect the shape of a propeller. Each of the individual cutting edges 20 is formed as a single piece, so that the cutting edges 20 have one cutting element 20. The full cutting surface is attained by an overlap of about 5% to 15% of the individual cutting edges 20 in the rotational representation.

An additional guiding element 30 having helical shape is moreover formed at the superficies 10, which essentially extends in a helical manner from the pole 12 to the equator 14, the guiding element 30 being interrupted in the region around the cutting edges 20 and traversing the region between any two cutting edges 20 at least twice.

Openings 22 are formed in the superficies 10 between the cutting edges 20 and the guiding element 30 in order to eliminate the chips into the hollow interior space 50. During the cutting operation, the tool represented turns counterclockwise while each cutting edge 20 has a plurality of notches 24 serving as chip breakers, in such a way that the chips of a workpiece that is not represented, which are cut up by the cutting edges 20, will be eliminated through the openings 22 into the hollow interior space 50, the length of the notches 24 increasing from the pole 12 to the equator 14. Further, a bearing shaft 40 which extends through the hollow interior space 50 is fastened at the superficies 10, and particularly at the pole 12, constituting both the axis of rotation and the axis of symmetry of the tool. The bearing shaft 40 can be seen in part in the hollow interior space through the openings 22.

FIG. 2 presents a lateral view of the tool embodiment of FIG. 1, showing in particular the shape of the hemispherical superficies 10.

FIG. 3 presents a sectional view of a cutting element 20 in the region of the pole of the superficies 10 of the tool according to the invention of FIGS. 1 and 2. A clearance angle γ is subtended between the superficies 10 and the cutting surface 26 of the cutting element or cutting edge 20 turned toward the workpiece. On the other hand a rake angle α is subtended between the superficies 10 and the cutting surface 28 of the cutting element or cutting edge 20 turned away from the workpiece.

In addition, the clearance angle γ and the rake angle γ of the cutting element 20 are presented in FIG. 4 in the region of the equator 14 of the superficies 10 of the advantageous embodiment of the tool of FIGS. 1 and 2. Compared to FIG. 3, the clearance angle γ is smaller in FIG. 4, from which it can be seen that the amount of material removed by the cutting edge 20 will decrease from the pole 12 of the superficies 10 toward the equator 14 of the superficies 10 owing to the decrease of clearance angle γ.

On the other hand, the rake angle a in FIG. 4 is larger than that in FIG. 3, in order to adjust the volume of material removed as a function of the radius. It follows that advantageously, the rake angle a of the cutting edge 20 which is subtended between the superficies 10 and the cutting surface 28 of the cutting element or cutting edge 20 turned away from the workpiece increases from the pole 12 of the superficies 10 toward the equator 14 of the superficies 10.

It can further be seen from FIG. 2 that the clearance angle γ of the cutting edge 20 decreases continuously from the pole 12 of the superficies 10 toward the equator 14 of the superficies 10, since from the pole 12 of the superficies 10 toward the equator 14 of the superficies 10, the cutting edge 20 continuously increases in width.

FIG. 5 is a graphical representation of cutting performance as a function of tool diameter, the x-axis representing the diameter of the tools and the y-axis representing the cutting performance of the tools. Curve 70 represents the cutting performance of a tool according to the invention plotted against the diameter while curve 60 is the cutting performance of a conventional tool plotted against the diameter, the dashed line indicating a cutting performance of 100%. The intercept of curves 60 and 70 on the x-axis indicates the pole 12 of the tools, the cutting rate at the pole 12 of the tools being zero since the distance from the axis of rotation is zero at the pole 12.

It can be seen from the graphical representation of FIG. 5 that the cutting performance of the tool according to the invention is higher than that of the conventional tool, since the area under the curve 70 is larger. Further, since the clearance angle γ of the cutting edge 20 decreases toward the periphery or pole 12 of the tool, the tendency of drift of the tool according to the invention is reduced as compared to that of conventional tools, since the largest cutting yield of the tool according to the invention is closer to the pole 12 of the superficies 10, as compared to conventional tools. This implies that, as compared to conventional tools, the tool according to the invention when advancing appropriately in the direction of the axis of rotation is autocentering during the cutting operation.

Moreover, the guiding element present in a further embodiment of a tool according to the invention that is not shown, for which only the differences relative to the embodiment shown in FIGS. 1 to 4 will be discussed, has a radial or helical cutting edge and a radial or helical opening cooperating therewith, in the superficies 10, serving to eliminate the chips into the hollow interior space 50, while more particularly the clearance angle γ of the helical cutting edge that is subtended between the superficies 10 and the cutting surface of the cutting element turned toward the workpiece decreases from the pole 12 of the superficies 10 toward the equator 14 of the superficies 10. The helical cutting edge moreover has a plurality of intersections, at least two, with the cutting edges 20 that are distributed in the shape of propellers on the superficies, the points of intersection between the helical cutting edge and the propeller-shaped cutting edges 20 serving as chip breakers. Moreover, the openings 22 of the propeller-shaped cutting edges 20 overlap with the helical opening, so that the superficies 10 of the tool is built up, merely from the helical cutting edge and the propeller-shaped cutting edges 20, while the propeller-shaped cutting edges 20 are more particularly interconnected by bridges for stabilization in the region of the equator 14.

According to a further embodiment that is not shown, three cutting edges are distributed over the superficies, the individual cutting edges being built up from cutting elements arranged between concentric circles of the superficies and having bent shape.

It has been shown by the preceding description that manifold variants and modifications of the initial embodiment that has been presented can be realized without departing from the scope of the invention. For instance, the cutting edge extending from the pole of the superficies to the equator of the superficies can also be built up from a multitude of independent cutting elements. Furthermore, a tool according to the invention can be fixed in a chuck while the workpiece is rotated. Moreover, the superficies of the tool can have a shape which does not correspond to an ideal hemisphere but is similar to a hemisphere or corresponds to a part of a hemisphere that does not extend all the way to the equator.

Furthermore, the guiding element can be built up from circular elements arranged on the superficies or from a multitude of individual segments.

What is claimed is:

1. Surgical tool to create a recess for an artificial joint in cartilaginous and/or bony tissue, and particularly for an artificial acetabulum in hip-joint bones, having an essentially hemispherical surface and a hollow interior space bounded by this surface, where in the surface there are formed at least one cutting element extending from the pole of the surface and having at least one cutting surface turned towards a workpiece and one cutting surface turned away from the workpiece, as well as one opening in the surface cooperating therewith to evacuate chips towards the hollow interior space, characterized in that a clearance angle γ of the cutting element subtended between the surface and the cutting surface turned towards the workpiece decreases from the pole of the surface toward the equator of the surface.

2. Surgical tool according to claim 1, characterized in that the clearance angle γ decreases in steps as a function of distance from the axis of rotation.

3. Surgical tool according to claim 2, characterized in that the cutting elements have notches.

4. Surgical tool according to claim 1, characterized in that the clearance angle γ decreases continuously as a function of distance from the axis of rotation.

5. Surgical tool according to claim 4, characterized in that the cutting elements have notches.

6. Surgical tool according to claim 1, characterized in that the clearance angle γ is calculated from arc tan $h_c/2 r\pi$, while the maximum depth of advance $h_c$ of the cutting edge into a workpiece is essentially constant over the entire periphery of the cutting edge.

7. Surgical tool according to claim 6, characterized in that the cutting elements have notches.

8. Surgical cutting tool according to claim 1, characterized in that a rake angle α of the cutting element which is subtended between the surface and the cutting surface turned away from the workpiece increases from the pole of the surface toward the equator of the surface.

9. Surgical tool according to claim 8, characterized in that the cutting elements have notches.

10. Surgical tool according to claim 1, characterized in that the cutting element is helically bent.

11. Surgical tool according to claim 10, characterized in that the cutting elements have notches.

12. Surgical tool according to claim 1, characterized in that two to seven cutting elements uniformly distributed over the surface extend from the pole towards the equator.

13. Surgical tool according to claim 12, characterized in that the cutting elements have notches.

14. Surgical tool according to claim 1, characterized in that three to five cutting edges uniformly distributed over the surface extend from the pole toward the equator.

15. Surgical tool according to claim 14, characterized in that the cutting elements have notches.

16. Surgical tool according to claim 1, characterized in that the cutting elements have notches.

17. Surgical tool according to claim 1, characterized in that at least one additional guiding element having a cutting function is formed while extending radially with respect to the surface.

18. Surgical tool according to claim 17, characterized in that the guiding element essentially extends in helical form from the pole to the equator.

19. Surgical tool according to claim 18, characterized in that the guiding element has a radial cutting edge and a radial opening in the surface cooperating therewith, to eliminate chips into the hollow internal space.

20. Surgical tool according to claim 17, characterized in that the guiding element has a radial cutting edge and a radial opening in the surface cooperating therewith, to eliminate chips into the hollow internal space.

21. Surgical tool according to claim 17, characterized in that the guiding element intersects at least twice with each of the two to seven cutting edges.

22. Surgical tool according to claim 1, characterized in that for rotation around the axis of symmetry which forms the axis of rotation, a bearing shaft extending through the hollow internal space is fastened at the surface.

* * * * *